(12) United States Patent
Bridenbaugh et al.

(10) Patent No.: US 8,680,261 B2
(45) Date of Patent: *Mar. 25, 2014

(54) METHODS FOR PURIFYING NUCLEIC ACIDS

(76) Inventors: Robert Bridenbaugh, Milbrae, CA (US); Warren Dang, Alameda, CA (US); Lee B. Bussey, San Mateo, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/796,961

(22) Filed: Jun. 9, 2010

(65) Prior Publication Data

US 2010/0248336 A1    Sep. 30, 2010

Related U.S. Application Data

(63) Continuation of application No. 09/121,798, filed on Jul. 23, 1998, now Pat. No. 7,807,822, which is a continuation-in-part of application No. 08/691,090, filed on Aug. 1, 1996, now Pat. No. 6,011,148.

(51) Int. Cl.
*C07H 1/06* (2006.01)
*C12P 19/34* (2006.01)

(52) U.S. Cl.
USPC ........................................ 536/25.4; 435/91.1

(58) Field of Classification Search
None
See application file for complete search history.

(56) References Cited

U.S. PATENT DOCUMENTS

| 4,621,061 | A | * | 11/1986 | Puhler et al. | 435/91.4 |
| 4,699,717 | A | * | 10/1987 | Riesner et al. | 536/25.4 |
| 4,830,969 | A | * | 5/1989 | Holmes | 435/259 |
| 5,837,529 | A | * | 11/1998 | Wan et al. | 435/259 |
| 6,011,148 | A | * | 1/2000 | Bussey et al. | 536/25.4 |

OTHER PUBLICATIONS

Marquet et al., BioPharm. (Sep. 1995), pp. 26-37.*
Maniatis, Molecular Cloning, A laboratory manual, Cold Spring Harbor Laboratory, 1982, pp. 86, 87, 90, 91.*

* cited by examiner

*Primary Examiner* — Nancy T Vogel
(74) *Attorney, Agent, or Firm* — D. Benjamin Borson; Borson Law Group, PC

(57) ABSTRACT

Methods are provided for producing highly purified compositions of nucleic acids by using a highly streamlined and readily automated process. The methods use static mixers for lysing cells and precipitating debris, following by centrifugation and ion exchange chromatography. The process may include a purification step using tangential flow ultrafiltration. A scaleable process for producing pharmaceutical grade plasmid DNA, useful for gene therapy, is provided.

7 Claims, 5 Drawing Sheets

METHODS FOR PURIFYING NUCLEIC ACIDS

CLAIM OF PRIORITY

This United States Utility Patent Application filed under 35 U.S.C. §120 and 37 C.F.R. 1.53(b) is a continuation of U.S. patent application Ser. No. 09/121,798, filed Jul. 23, 1998, now U.S. Pat. No. 7,807,822 which is a continuation-in-part of U.S. patent application Ser. No. 08/691,090, filed Aug. 1, 1996, now U.S. Pat. No. 6,011,148, issued Jan. 4, 2000. The above application and patent are each herein incorporated fully by reference.

FIELD OF THE INVENTION

The invention relates to methods for producing high purity nucleic acids. The invention relates in particular to methods for preparing pharmaceutical quality nucleic acids.

BACKGROUND OF THE INVENTION

Since the advent of recombinant DNA, methods have been developed and improved for the purification of DNA and RNA to further molecular biology research. While these methods have allowed considerable study of nucleic acids in research environments, they have not addressed issues involved in the human clinical use of purified nucleic acids such as is required for many current gene therapy protocols.

Gene therapy involves the introduction of nucleic acid into a patient's cells, which, when expressed, provide a therapeutic benefit to the patient. Examples include the introduction of an exogenous, functional gene to correct a genetic defect in a patient carrying a defective gene or to compensate for a gene that is not expressed at sufficient levels. Other examples include the introduction of mutant genes, antisense sequences or ribozymes to block a genetic function, e.g., in the treatment of viral infections or cancer.

Much of the focus in gene therapy has been on using viral vectors, especially retroviral vectors, for introducing exogenous nucleic acid into a patient's cells. To date, most of these protocols have been for ex vivo gene therapy, in which the patient's cells are first removed from the patient, genetically modified ex vivo, and then returned to the patient. The alternative to ex viva gene therapy is in vivo gene therapy. In vivo gene therapy refers to the introduction of exogenous genetic capability directly to the patient where it is taken up by the target cells, which then express the introduced gene to produce a therapeutic product. Viral vectors have been used for in vivo gene therapy although their use is associated with a number of drawbacks, e.g. immunogenicity of the viral vector and safety concerns such as insertional mutagenesis or viral contamination.

Other means of in vivo gene delivery include the introduction of naked DNA into the target issue of interest, or the use of lipid-mediated DNA delivery. Typically, introduction of naked DNA will be used when the exogenous genetic capability is to be introduced directly into the target issue. By complexing with liposomes or lipids, DNA is compacted, allowing systemic delivery of the lipid/DNA complexes to various tissues of interest. See PCT patent application WO 93/25673. Lipid/DNA complexes can be targeted to particular tissues by altering the lipid composition, lipid/DNA ratio, mode of delivery, etc.

For any application in which nucleic acid is introduced into a patient, there is a need to produce highly purified, pharmaceutical grade nucleic acid. Such purified nucleic acid must meet drug quality standards of safety, potency and efficacy. In addition, it is desirable to have a scaleable process that can be used to produce large quantities of DNA, e.g., in the range of 100s of milligrams to 100s of grams. Thus, it is desirable to have a process for producing highly pure nucleic acid that does not use toxic chemicals, known mutagens, organic solvents, or other reagents that would compromise the safety or efficacy of the resulting nucleic acid, or make scale-up difficult or impractical. It is also desirable to prepare nucleic acids free from contaminating endotoxins, which if administered to a patient could elicit a toxic response. Removal of contaminating endotoxins is particularly important where the nucleic acid is purified from gram negative bacterial sources, e.g. plasmid or bacteriophage DNA, which have high levels of endotoxins.

The invention described below meets these needs and provides other related advantages as well.

SUMMARY OF THE INVENTION

The present invention is directed to a method for purifying a nucleic acid from cells.

The present invention provides automatable methods for purifying plasmid DNA from cells. The methods involve use of a static mixer to mix the cells with a lysis solution to provide controlled, gentle mixing of the cells with the lysis solution. Static mixers are further used to mix the resulting lysis mixture with a precipitation solution to precipitate out cell debris and other contaminants, including chromosomal DNA. This is typically followed by an additional step of centrifugation to remove the precipitated material. The methods of the invention are sufficient to provide a purified DNA solution that does not require complex purification steps (e.g., ultrafiltration) prior to application to an ion exchange chromatography to produce a final product.

When desired, the methods can be readily automated according to well known methods by including appropriate computer controls of steps in the process to ensure desired results. The invention also provides particular conditions by which the methods can be used to prepare plasmid DNA in an automated manner.

DEFINITIONS

"Diafiltration" is a mode of operating an ultrafiltration system in which the retentate is continuously recycled and diluted with fresh wash solution to replace that removed as permeate. Diafiltration will generally provide a cleaner separation of macromolecules retained in the retentate sample while the smaller molecules pass through into the filtrate. It may also be used to perform solvent removal or buffer exchange in the same step. "Continuous diafiltration" refers to the continuous addition of fresh wash buffer as filtration takes place. "Discontinous diafiltration" refers to the repeated steps of concentrating the sample by ultrafiltration, and rediluting with buffer.

"Episomal nucleic acids" are extrachromasomal nucleic acids. Such nucleic acids include DNA, RNA and chimeric DNA/RNA molecules, and may be from any biological source including eukaryotic and prokaryotic cells, or may be synthetic. Nucleic acids that may be purified include ribosomal RNA, mRNA, snRNAs, tRNA, plasmid DNA, viral RNA and DNA, synthetic oligonucleotides, ribozymes, and the like. Preferred are viral nucleic acids, and plasmid DNAs. Of particular interest are plasmid DNAs encoding therapeutic genes. By "therapeutic genes" is intended to include functional genes or gene fragments which can be expressed in a suitable host cell to complement a defective or under-expressed gene in the host cell, as well as genes or gene fragments that, when expressed, inhibit or suppress the function of a gene in the host cell including, e.g., antisense sequences, ribozymes, transdominant inhibitors, and the like.

Thus, e.g., viral DNA or RNA may be purified from prokaryotic or eukaryotic viruses, in which the viral particles are initially purified from cultures or cells permissive for viral infection in accordance with conventional techniques, e.g., from bacterial, insect, yeast, plant or mammalian cell cultures. Extrachromosomal DNAs include autonomously replicating DNAs from a variety of sources including, e.g., mammalian cells (see, e.g., Yates et al., *Nature* (1985) 313:812-815; Heinzel et al., *Mol. Cell. Biol.* (1991) 11(4): 2263-2272), plant cells, yeast cells (e.g., 2 µm plasmids), and prokaryotic cells. Plasmid DNA isolated from prokaryotic cells include naturally occurring plasmids as well as recombinant plasmids encoding a gene of interest including, e.g., marker genes or therapeutic genes.

A "gel-layer," refers to a thin gelatinous layer of biomolecules that can form on or in an ultrafiltration membrane. The gel layer is generally a cohesive, adherent layer of constant solute concentration, also commonly referred to as concentration polarization. It usually will have some degree of hydraulic permeability depending on the nature of the solute forming the layer. "Gel-layer controlled" ultrafiltration refers to filtration conditions where the gel layer becomes the limiting factor to filtrate flow rate, and further pressure increases have little or no effect. By contrast, "membrane controlled" conditions are those in which the filtrate flow rate is controlled by the permeability of the membrane and the applied pressure.

An "open channel" filter is one which does not have a screen in the feed channel. By contrast, a "screen channel" or "closed channel" is a filter that has a screen in the feed channel.

"Permeate" refers to that portion of a sample that passes through the ultrafiltration membrane, and is also termed the "filtrate."

"Retentate" refers to that portion of a sample that does not pass through the ultrafiltration membrane.

"Static mixer" refers to any flow through device which provides enough contact time between two or more liquids to allow substantially complete mixing of the liquids. Typically, static mixers contain an internal helical structure which allows the liquids to come in contact in an opposing rotational flow and causes them to mix in a turbulent or laminar flow. Such mixers are described, for instance, in U.S. Pat. No. 3,286,922.

"Tangential flow" or "cross-flow" filtration refers to a filtration process in which the sample solution circulates across the top of the membrane, while applied pressure causes solute and small molecules to pass through the membrane.

"Ultrafiltration" refers to a technique to separate particles by filtration through membranes having pore sizes ranging from about 0.001 µm to about 0.05 µm. Ultrafiltration membranes typically have a molecular weight cut-off (MWCO) in the range of 1,000 to 1,000,000 daltons. The MWCO typically is defined as the molecular weight of the globular solute which is 90% retained by that membrane. See Filtron Catalog, 1995/96, p. 5. The actual molecular weight of particles that pass through or are retained by a membrane will depend on the size as well as the conformation and charge of a given molecule, the nature of the membrane pore or matrix, and the conductivity and pH of the solution.

DETAILED DESCRIPTION OF THE PREFERRED EMBODIMENTS

The present invention provides a highly streamlined process for the purification of plasmid DNA, which process is readily scalable and yields high quality DNA. The process minimizes complex or expensive purification steps, thus minimizing cost and allowing an increase in throughput. It is also an advantage of the invention that the process is readily automated. The process is particularly suitable for providing pharmaceutical grade plasmid DNA at commercial sale.

In the methods of the invention, static mixers are used to mix certain solutions, particularly where gentle and complete mixing is desired. Such devices are useful, for instance, in isolating plasmid DNA from lysed bacterial cells, or for precipitating cell debris, proteins, and chromosomal DNA after lysis. During these procedures, the mixing should be complete to maximize recovery and should be relatively quick to maintain DNA integrity. If mixing is too vigorous, however, genomic DNA can be sheared and may contaminate the plasmid preparation. Static mixers are advantageous in these applications because substantially complete mixing can be obtained while minimizing shear of genomic DNA. In addition, lysis is typically carried out in caustic solutions such as alkali, which can affect the quality of the final preparation. Since static mixers allow continuous flow, the time in contact with these solutions can be carefully controlled.

Figure 1A:
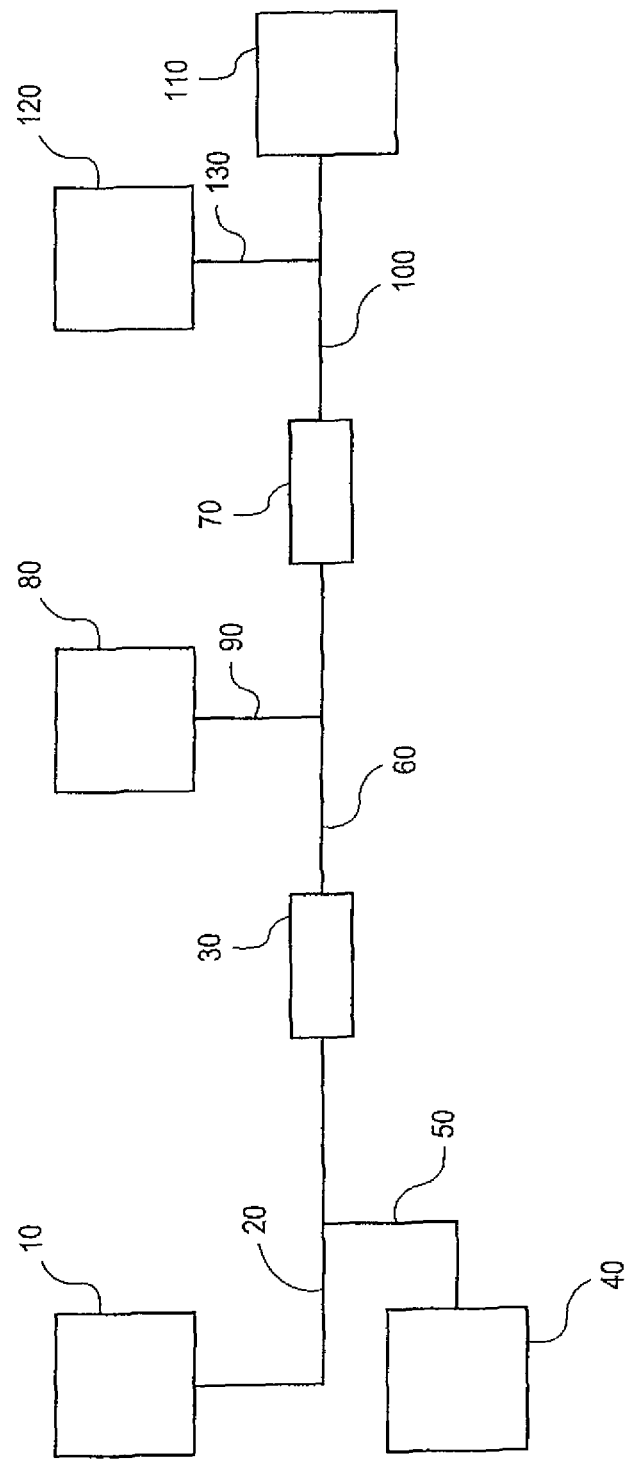
FIG. 1A is a schematic diagram of a system of the present invention.

FIG. 1A is a schematic diagram of a system of the present invention. The illustrated system can be conveniently used for isolation of plasmid DNA from bacterial cells. The various solutions are flowed through the mixers and lines of the system using pumps (e.g., peristaltic pumps) or pressure according to standard techniques. A tank 10 containing cells is linked by line 20 to static mixer 30. The cells (typically *E. coli*) are usually first pelleted from a culture according to well known techniques. After pelleting, the cells to a density of up to 75% solids, they can be frozen for future plasmid preparation or used directly in the methods of the invention. Typically, the cells are resuspended in a suitable solution (e.g., 25 mM Tris-HCl, pH 8, 10 mM EDTA, 50 mM dextrose) at room temperature with stirring at 150 rpm for 1 h. Typically, the cells are resuspended in about 5 liters per kilogram (kg) of cell paste. Alternatively, static mixers can be used for this purpose. RNase can also be added at this time (e.g., 24,000 Kunitz units RNase/kg cell paste) to decrease the amount of RNA in later steps.

Tank 40 containing lysis solution is connected to line 20 through line 50. The lysis solution can be any solution suitable for lysis of the cells being used. Lysing agents include alkali, detergents, and enzymes. Although organic solvents can be used for this purpose, the use of such solvents pose safety and regulatory concerns due to the possibility of trace amounts in the final product. In addition, such solvents are toxic and inflammable, and pose serious risk and disposal problems if used in the quantities required for large scale purification. A typical lysis solution will be 0.2N NaOH/1% SDS, and approximately 10 liters per kg of cell paste is used.

The lysis solution contacts the cell solution in line 20 and the lysis mixture proceeds to static mixer 30. The intersection between lines 20 and 50 can be adjusted so that the cell solution and lysis solution enter the static mixer 30 essentially simultaneously. The degree of mixing is controlled by varying the linear velocity or flow rate of the solution through the mixer, the type of mixer used, the diameter of the mixer, and the number of elements in the mixer. For instance, in the preparation of plasmid DNA from bacterial cells a laminar flow static mixer from Kenics is conveniently used and is preferred to turbulent flow static mixers from Kenics or other vendors. The linear velocity used depends on the manufacturer and type of mixer; this controls the Reynolds number achieved and how gentle the mixing is. Turbulent mixers can sometimes be used at low velocities, such that the shear rate is low enough to avoid damage to the plasmid DNA. However, the shear rate is more sensitive to changes in linear velocity in the turbulent flow mixers, making them a less robust choice for consistent large scale production.

A linear velocity of 0.38 to 2.3 feet per second gives acceptable product quality when using a 2" diameter, 24 element, laminar flow static mixer from Kenics with an overall length of about 6 feet (corresponding to a Reynolds number from 50 to 500). This linear velocity range permits sufficient mixing to thoroughly lyse the cells and yet not be so high that genomic DNA is sheared to a size that is problematic in later purification steps. At a 0.7 feet per second linear velocity the flow rate in a 2" diameter mixer is typically 22 liters per minute.

The lysis mixture exiting the static mixer 30 then flows through line 60 to static mixer 70. A tank 80 containing a precipitating solution is connected through line 90 to line 60. The precipitating solution is used to precipitate proteins, chromosomal DNA and cell debris. Typically, the solution will contain potassium acetate. A suitable precipitating solution is 3M potassium acetate, adjusted to pH 5.5, with acetic acid (5M acetate final). As with the first static mixer, the intersection between lines 60 and 90 can be adjusted so that the lysis mixture and the precipitation solution enter the static mixer 70 essentially simultaneously. Similar linear velocities are used to ensure sufficient mixing to thoroughly precipitate the proteins and cellular debris and yet not be so high that genomic DNA is sheared to a size that is problematic in later purification steps. Typically, approximately 5 liters of precipitating solution is used per kg of cell paste.

After exiting static mixer 70, the precipitating solution flows through line 100 to centrifuge 110. In some embodiments, a tank 120 containing a buffer solution is connected to line 100 through line 130. The buffer solution is used to raise the pH of the solution to minimize acid catalyzed de-purination of the DNA and to condition the material for binding onto the anion exchange column, e.g., a pH is the range of 6 to 9, preferably from 7 to 8.5. A useful buffer solution for this purpose is 1 M Tris. More concentrated solutions can be used to adjust the pH, however the use of a more diluted buffer solution has other benefits. A diluted buffer reduces the viscosity of the solution going into the centrifuge to yield better clarity. It also decreases the ionic strength of the solution, such that it can be loaded directly onto the anion exchange column.

The target ionic strength for loading onto an anion exchange column depends on the anion exchange resin used. The ionic strength will be less than that at which the DNA binds the resin at sufficient capacity—e.g., greater than 0.5 grams of DNA per liter of resin.

The precipitation mixture flows into centrifuge 110 to remove the precipitated material. The precipitation mixture may be put directly into the centrifuge or may be buffered before centrifugation. The centrifugation is typically carried out at less than 15,000 g in a disk stack or decanting centrifuge, such as an Alfa Laval MBUX 510. Alternately, the outflow of the static mixer may be connected directly into the centrifuge to minimize the need for an additional tank and to minimize the processing time. Depending on the cells processed, the fermentation conditions, and the centrifuge used, it may be more beneficial to add the buffering solution at the outflow of the centrifuge to achieve optimal clarity. Those conditions may be determined empirically. While it is usually preferable to neutralize prior to centrifugation, in some cases neutralization may dissolve some precipitate, which then will not be removed by centrifugation and, therefore, will remain as a contaminant. In that case, it is preferable to add the neutralization solution after centrifugation.

It is an advantage of the present invention that cell lysis, precipitation and clarification can be performed in a continuous, automated process by use of static mixers and centrifugation, with appropriate adjustment of flow rates. The flow rate must be sufficient to achieve adequate mixing, but should not be in excess of the rate allowing sufficient residence time in the centrifuge to achieve the separation, or to shear genomic DNA. The flow rate should not be so slow that residence time in the centrifuge is too long, which can permit extended contact time with solutions, allowing degradation of the product by endonucleases or alkali. Appropriate sizing of the static mixers, pumps and centrifuge, and selection of flow rate will allow continuous operation of the process, while maximizing yield and quality. Preferably, the process is automated to ensure reproducibility. An example of conditions allowing continuous operation is described in Example 4 below. Appropriate assays for monitoring product quality, which are, therefore, useful in optimizing process conditions, are also described in the Examples that follow.

Ion exchange chromatography may be used to further purify the nucleic acid, particularly from contaminating endotoxin, trace proteins, and residual cellular contaminants. A chromatography column is packed with an anion exchange chromatography resin. The optimal capacity of the column will be determined empirically based on the resin used and the size of nucleic acid to be purified.

Ion exchange chromatography resins are commercially available, including from EM Separations (Gibbstown, N.J.), BioSepra (Marlborough, Mass.), Polymer Laboratories (Amherst, Mass.), Perseptive Biosystems (Cambridge, Mass.), Toso Haas (Montgomeryville, Pa.) and Pharmacia (Uppsala, Sweden). For most plasmid DNAs, preferred resins are those with no pore or with a large pore size, e.g., greater than 1000 Å, preferably around 3000 Å to 4000 Å; with a medium bead size, e.g., about 20 to 500 µm diameter; that do not leach matrix components. Ideally, the resin is also washable, e.g., with sodium hydroxide to allow repeated use.

A chromatography column is packed with an anion exchange chromatography resin. The optimal capacity of the column is determined empirically based on the resin used and the size of the nucleic acid to be purified. The column is packed under low pressure, typically less than about 0.7 bar. The pressure will depend on the resin used, and will usually be according to the manufacturer's specifications. Normal column operating pressure may be lower where the resin pore size is smaller, to limit trapping of the nucleic acid in the resin pores. Thus, for resins without pores, column operating pressure may be increased. The column is packed at about twice the anticipated flow rate in accordance with conventional techniques.

The nucleic acid sample is loaded onto the column in a loading buffer comprising a salt concentration below the concentration at which the nucleic acid would elute from the column. Typically, the salt concentration will be about 10 to 50 mS/cm, depending on the resin used. For weaker anion-exchange resins, a lower conductivity solution will be used, whereas for stronger anion-exchange resins, a higher conductivity solution will be used. The column will then be washed with several column volumes of buffer to remove those substances that bind weakly to the resin. The nucleic acid is then eluted from the column using either one or more step increases in the saline concentration or a shallow continuous saline gradient according to conventional methods, e.g., using up to 1.5M NaCl in a Tris (pH 8.5) buffer. Collection of the nucleic acid from the step elution method is accomplished by directly pooling the plasmid into a vessel, based on absorbance, conductivity, volume or time. For eluant from the continuous gradient method, similar monitoring can be used or sample fractions can be collected and analyzed. For intermediate scale preparations (e.g., from about 100 mg to about 3 grams nucleic acid), fractions will typically be at least 50 ml to 2 liters where the nucleic acid peak is expected, then increased in volume past the expected peak. Analytical determinations of nucleic acid yield and purity are performed on each fraction. In addition, *Limulus* ameobocyte lysate (LAL) analyses may be performed on each fraction to determine residual endotoxin levels in each fraction. Fractions containing high levels of nucleic acid and low endotoxin are pooled. For large scale preparation, step elution is preferred. For example, when using a resin as described in the Examples herein, the plasmid DNA loading solution conductivity is about 50 mS/cm, and the plasmid DNA is eluted at about 59 mS/cm. The resulting nucleic acid sample may again be filtered through 0.2 μm filter to control the number of microbial organisms.

The preferred method for purifying plasmid DNA at larger scale is to load the lysate directly onto the ion exchange chromatography column after clarification and neutralization. This can be done to avoid additional purification steps, and greatly simplifies the process. In this "direct load" process, after the lysate is clarified by centrifugation, further debris may be removed by, e.g., decanting through a depth filter. The pH and conductivity is then adjusted to the appropriate values, which depend on the anion exchange resin used. A preferred resin is TMAE Fractogel 650M resin (EM Separations Technology, Wakefield, R.I., US Associate of E. Merck, Darmstadt, Germany). TMAE Fractogel 650M is a tentacle ion exchanger having trimethylaminoethyl functional groups (TMAE) covalently attached to hydroxyl groups of a synthetic methacrylate based polymeric resin backbone. With this resin, the pH is adjusted to about 8.5 and the conductivity is adjusted to less than about 50 mS/cm. This can be accomplished by adding about 0.6 volumes of 1M Tris per volume of lysate or by diluting 0.25-0.3 fold with water, then adding Tris base powder to a final concentration of 0.62M.

In this embodiment, the ion exchange column is packed and operated at 1 column bar pressure, at a linear flow velocity of up to 300 cm/hr. The column is equilibrated in a Tris buffered, saline solution with a conductivity of about 50 mS/cm. After loading the conditioned lysate, the column is washed with sufficient volumes of 50 mS/cm buffer to remove non-binding impurities, e.g. usually greater than three column bed volumes of buffer, and preferably about five column bed volumes are used or until an $A_{260}$ reading returns to baseline. Weakly bound impurities (proteins, RNA and host DNA) are eluted from the column with a buffer that is high enough in saline concentration to remove impurities, yet not elute the plasmid DNA. Usually, at least three column bed volumes of pre-elution buffer are used, with a conductivity of typically 56 mS/cm. The plasmid DNA is then eluted from the column by increasing the saline concentration further to a conductivity of about 59 mS/cm. The plasmid DNA elutes as a single peak and can be pooled based on absorbance, time or volume of buffer used. The saline concentration chosen for the pre-elution and elution buffers depends on the nature of the plasmid, plasmid impurities, and the resin used. Additionally, the saline concentration of the elution buffer is optimized to elute the plasmid DNA in the smallest volume, yet still resolve it from other plasmid degradation products.

In some embodiments, ultrafiltration may be used before the step of ion exchange chromatography. Typically, ultrafiltration is carried out as described in WO 98/05673, which corresponds to U.S. Ser. No. 08/691,090, now U.S. Pat. No. 6,011,148, supra.

Figure 1B:
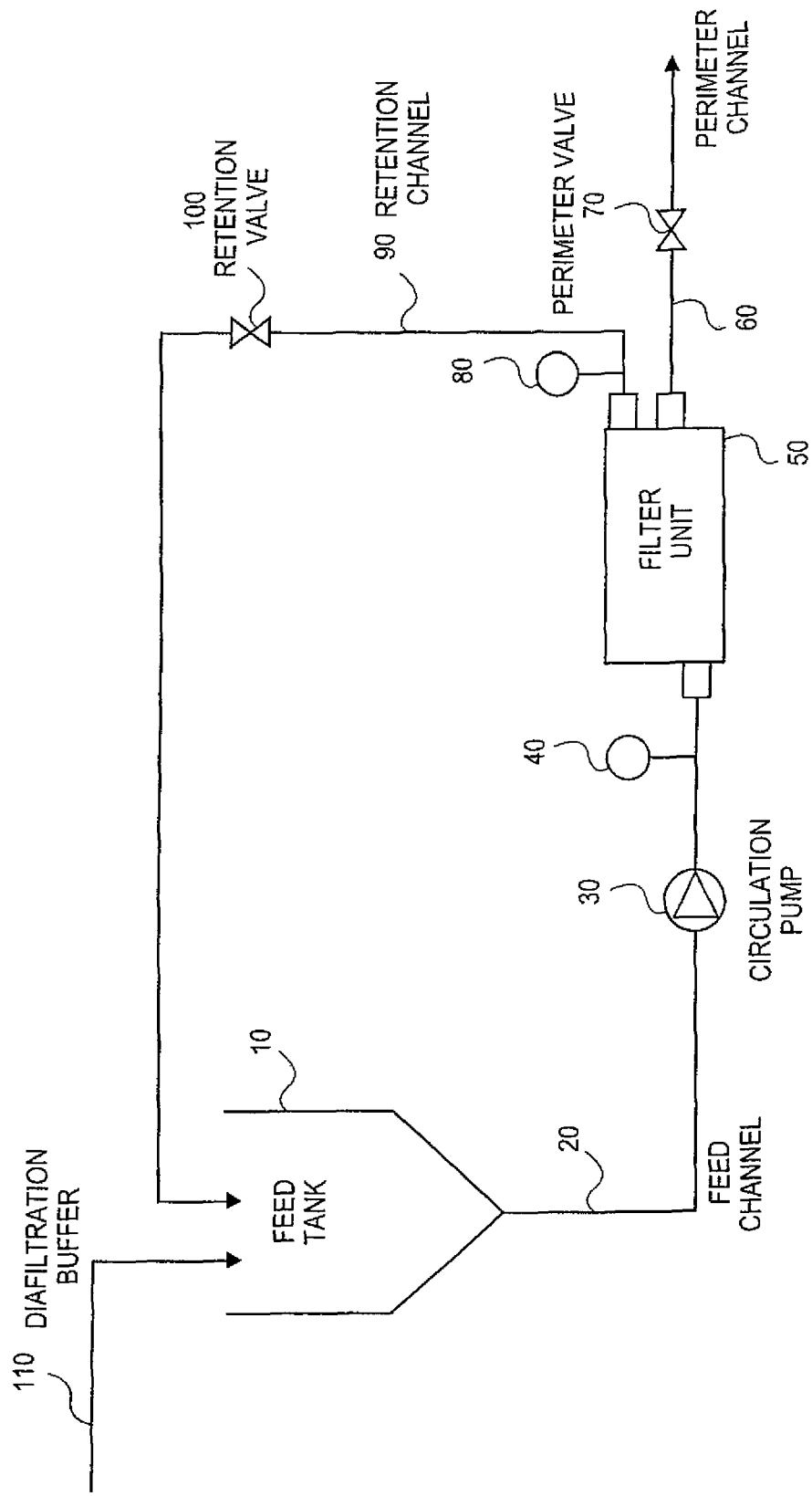
FIG. 1B is a schematic diagram of a tangential flow ultrafiltration process.

In brief, FIG. 1B provides a schematic diagram of a tangential flow ultrafiltration process. The feed tank 10 comprises the sample solution to be filtered. The solution enters the filtration unit 50 through the feed channel or feed line 20. The circulation pump 30, located in the feed line 20, controls the solution flow. The filtration unit 50 comprises the ultrafiltration membrane. Filtration through the ultrafiltration membrane separates the sample solution into a permeate solution and a retentate solution. The permeate solution exits the unit through the permeate channel or permeate line 60. Flow through the permeate channel may be controlled through a permeate valve located in the permeate channel 60. The retentate solution passes into the retentate channel or rentate line 90, which is circulated back into the feed tank 10. Pressure across the ultrafiltration membrane (transmembrane pressure or TMP) is measured by pressure detectors in the feed channel 40 and in the retentate channel 80. TMP is controlled by adjusting the retentate valve 100. When TFU is performed in diafiltration mode, diafiltration buffer 110 is added to the sample solution in the feed tank 10. When TFU is used to concentrate the sample solution, however, diafiltration buffer 110 is not added to the feed tank 10. System control can be manual or automated, with pressure transducers, flow meters, in-line conductivity meters, and other feedback loops.

The ultrafiltration membrane will be selected based on the size and conformation of the nucleic acid to be purified, and typically will have a molecular weight cut-off (MWCO) in the range of 1K to 1,000K Daltons. For many supercoiled plasmid DNAs, ultrafiltration membranes having a MWCO around 300 k to 500 k daltons may be used. For some larger plasmids, however, improved speed, purity and quality of the resultant DNA is obtained when larger MWCO membranes are used. Preferably, therefore, plasmid DNA with sizes ranging from about 2 Kb to 15 Kb are purified using ultrafiltration membranes having a MWCO of 300K daltons; plasmids ranging from about 15 Kb to about 50 Kb may be purified using membranes having a MWCO of 500K daltons; and plasmids of about 40 Kb or larger may be purified using membranes having a MWCO of 1,000K daltons. With some hollow fiber ultrafiltration devices, e.g., those with symmetric pores, larger nominal pore sizes may be used. For example, plasmid DNA of us to about 5 Kb can be purified using membranes having up to 500K daltons MWCO in a hollow fiber device.

Under these conditions, plasmid DNA will be retained in the retentate while contaminating substances including many proteins, cell membrane debris, carbohydrates, small degraded nucleotides, etc., pass through the membrane into the filtrate. Smaller nucleic acids, e.g., small synthetic oligonucleotides, may be purified using ultrafiltration membranes with a MWCO of around 1K to 5K daltons. For any nucleic acid to be purified, the optimal membrane pore size may be determined empirically using small scale devices, e.g., centrifugation devices, stirred cell devices, or small scale hollow fiber systems, available from a variety of commercial manufacturers. A manifold system may be used for optimizing parameters in process scale development. Commercial sources for ultrafiltration devices include Pall-Filtron (Northborough, Mass.), Millipore (Bedford, Mass.), and Amicon (Danvers, Mass.).

Many types of ultrafiltration devices useful in the present invention are commercially available including e.g., a flat plate device, spiral wound cartridge, hollow fiber, tubular or single sheet device. See Michaels et al., (1995). Preferably, the ultrafiltration unit is a flat plate device or hollow fiber device.

It has been found that shearing of the nucleic acid is minimalized if the filtration device used for TFU is an open-channel device. Screened channels inhibit formation of a gel layer and have been found to shear and decrease yield of the retained nucleic acid. Screen channels may be designed, however, having minimal compression of the screens such that the shearing and nucleic acid loss may be minimized.

The surface area of the ultrafiltration membrane used will depend on the amount of nucleic acid to be purified. Generally, about ten square feet of membrane is used per gram of nucleic acid. Thus, about five square feet of membrane is used per 200 to 800 mg nucleic acid; more typically, about five square feet of membrane is used for 400 to about 600 mg nucleic acid.

The membrane may be of a low-binding material to minimize adsorptive losses, and should be durable, cleanable and chemically compatible with the buffers to be used. A number of suitable membranes are commercially available, including e.g., cellulose acetate, polysulfone, polyethersulfone, and polyvinylidene difluoride. Preferably, the membrane material is polyethersulfone.

It has been found that higher yields and purities are obtained when a gel-layer is allowed to form at the membrane surface before starting TFU. The amount of time necessary for gel-layer formation may be determined empirically by monitoring the permeate solution for product loss, e.g., by HPLC analysis. The gel-layer is adequate once the product loss into the permeate is sufficiently low. Under preferred conditions, the gel layer acts as a second membrane barrier, which may cause nucleic acid molecules which would normally pass through the membrane to be retained. However, it is not necessary to perform the ultrafiltration under conditions, e.g., pressure and feed, that are fully gel-layer controlled. Thus, as used herein, filtration in the presence of a gel layer means that there is sufficient gel layer to cause additional solute retention beyond that resulting solely from the ultrafiltration membrane.

Typically, the gel layer is allowed to form for approximately 5 to 90 minutes, preferably around 20 to 60 minutes, depending on the device and size of the nucleic acid. For example, using a flat plate device to purify small plasmid DNAs (e.g., 2 Kb), the gel layer will be formed in about 60 to 90 minutes; for larger plasmid DNAs (e.g., 2-7 Kb), the gel layer will be formed in about 30 minutes. Using a hollow fiber device, the gel layer can be formed in approximately five to 30 minutes for most plasmid DNAs, or up to 45 minutes for plasmid DNAs less than about 2 Kb. After formation of the gel-layer, the permeate line 60 will be emptied into a waste receptacle and filtration allowed to proceed.

If a gel-layer is not allowed to form during an initial circulation period, product will usually be lost by leakage into the permeate solution. The amount of product loss will depend on the type of device used, the membrane MWCO and the total amount of nucleic acid in the sample. Thus, in circumstances where product yield is not critical, the filtration may be performed without an initial circulation period while the gel layer forms. In such cases, the gel layer may be allowed to form during the initial period of filtration, after which product leakage into the permeate solution will decrease and product will then be retained in the retentate solution. For example, since a gel layer can be formed in a hollow fiber device in a short time period (e.g., about five minutes for plasmid DNA of about 5 Kb, and about 150 mg DNA/sq. ft.), product loss during the initial period of forming the gel layer may not be significant and, therefore, re-circulation of the permeate solution into the feed tank while the gel layer forms may not be necessary.

Filtration will be performed using tangential flow to circulate the sample buffer as it crosses the membrane surface. During tangential flow filtration, pressure is applied across the membrane, which will allow smaller molecules to pass through the membrane while the retentate is recirculated. Typically, the flow rate will be adjusted to maintain a constant transmembrane pressure. Flow rate and pressure will usually fluctuate initially due to the formation of a gel layer. Generally, filtration will proceed faster with higher pressures and higher flow rates, but higher flow rate pressures are likely to cause shearing of the nucleic acid or loss due to passage through the membrane. In addition, various TFU devices may have certain pressure limitations on their operation. The pressure, therefore, may be adjusted according to the manufacturer's specification. For flat plate devices, the pressure is preferably from about 5 psi to about 30 psi, most preferably in the range of 10 psi to 20 psi. For most plasmid DNAs, 15 psi is preferred. Filtration will generally be performed in diafiltration mode. Optionally, the sample solution may initially be filtered without buffer addition until concentrated to a desired volume. Once concentrated, diafiltration buffer is added and filtration continues to wash the retentate solution of contaminating small molecules and remove unwanted solvents and salts. Diafiltration may be either continuous or discontinuous. Preferably, diafiltration is continuous, and performed until from about 510 to about 500 volume equivalents have been exchanged, preferably about 10 to 100 volume equivalents. Generally, more diafiltration will be performed with increased contaminants bound to the nucleic acids, depending upon the purity required.

Nucleic acids purified by tangential flow ultrafiltration may be used directly or may be further purified depending on the level and type of contamination in the starting sample and the desired use. Typically, the nucleic acid purified by tangential flow filtration will be greater than 90% pure, often 95% to 100% pure as analyzed by HPLC. The nucleic acid thus purified may be used for a number of applications, e.g., molecular biological applications such as cloning or gene expression, or for diagnostic applications using, e.g., PCR, RT-PCR, dendromer formation, etc.

For therapeutic uses, e.g. use in gene therapy, it may desirable to further purify the nucleic acid obtained from the tangential flow filtration step. When the tangential filtration step is used, the nucleic acid sample obtained from the tangential flow filtration step is subsequently filtered through a 0.2 µm filter, further purified using ion exchange chromatography, and, optionally, filtered again through a 0.2 µm filter. Desirably, the nucleic acid is further concentrated and diafiltered using tangential flow ultrafiltration, and filtered again through 0.2 µm filter as a final sterilization step.

Filtration through 0.2 µm filters, from certain vendors, can be used to remove endotoxin as well as microoganisms, while resulting in minimal nucleic acid loss. 0.2 µm filters are available from a variety of commercial sources including, e.g., Pall-Filtron (East Hills, N.Y.), Sartorius (Edgewood, N.Y.), and Gelman (Ann Arbor, Mich.). Ideally, the filter used will be one that binds endotoxin while allowing nucleic acid to pass through. Pall Ultipor $N_{66}$ filters and Sartorius Sartorpure GF filters have been found to remove substantial endotoxin with high yield of nucleic acid. Preferably, the nucleic acid solution is pre-filtered through a nominal 0.2 µm or a 0.45 µm or larger filter before filtration through an absolute 0.2 µm filter. Glass and nylon filters are preferred. Filters made for the removal of endotoxin, e.g., ion exchange filters, in many cases are not suitable for use with nucleic acid purification because the nucleic acid will bind to the filter.

For many applications it will be desirable to further purify the nucleic acid, lower the salt concentration of the resulting nucleic acid sample, concentrate the sample, and/or exchange the buffer to a more suitable buffer for subsequent uses. A final diafiltration step may be performed at this stage to achieve that result. If desired, a small MWCO ultrafiltration membrane may be used for this subsequent diafiltration step than used previously for purification, since the nucleic acid will be highly purified at this stage and predominantly small solute molecules will be passed through the membrane into the filtrate. For many plasmid DNAs, a 150K to 100K MWCO membrane may be used with a flat plate device, or a 100K MWCO membrane may be used with a hollow fiber device. Hollow fiber devices with about a 100K MWCO membrane are preferred at this stage, particularly when handling concentrated nucleic acid solutions, due to smaller hold-up volumes, increased flux, higher yields and shorter processing times. Where DNA purified according to the above protocol is to be complexed with a lipid carrier for use in gene therapy, it is desirable to exchange the DNA into a low conductivity buffer, preferably by diafiltration. A low-conductivity buffer is meant to include any buffer of less than about 10 mS, preferably less than about 1 mS.

At a variety of places in the above protocol, analytical determination of nucleic acid yield and purity are advantageously performed. Typically, such assays are performed before and after each purification step, as well as to each nucleic acid-containing fraction from, e.g., preparative ion exchange chromatography. Preferred means for performing these analytical determinations include HPLC analysis of purity, spectrophotometric estimation of yield, silver staining and SDS-PAGE for protein analysis, and agarose gel electrophoresis and Southern blotting for DNA analysis.

The following examples illustrate certain aspects of the above-described method and advantageous results. The following examples are shown by way of illustration and not by way of limitation.

EXAMPLES

Example 1

Preparation of p4119 DNA

Figure 2:
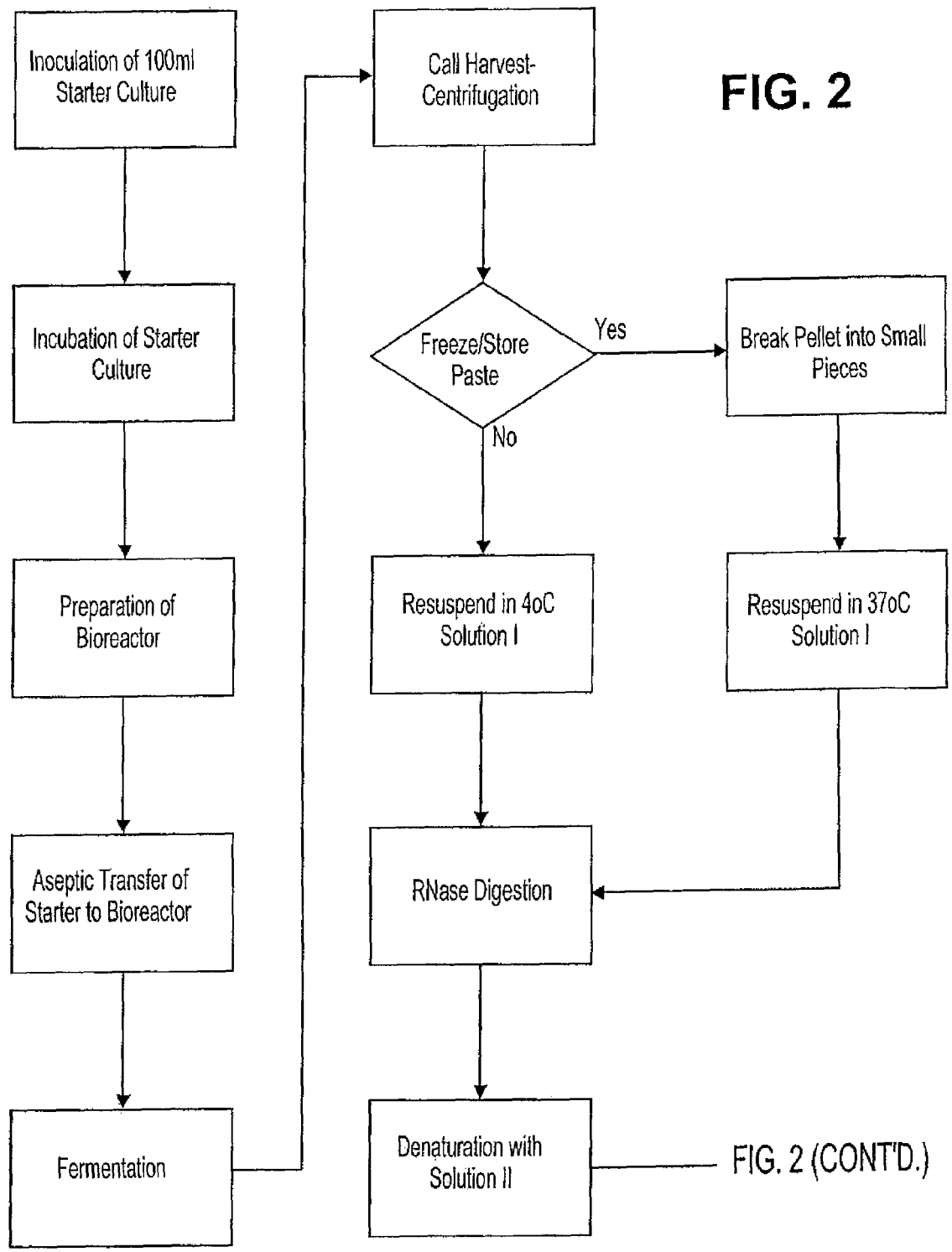
FIG. 2 illustrates a schematic diagram of large-scale plasmid DNA purification as described in Example 1.
Figure 2:
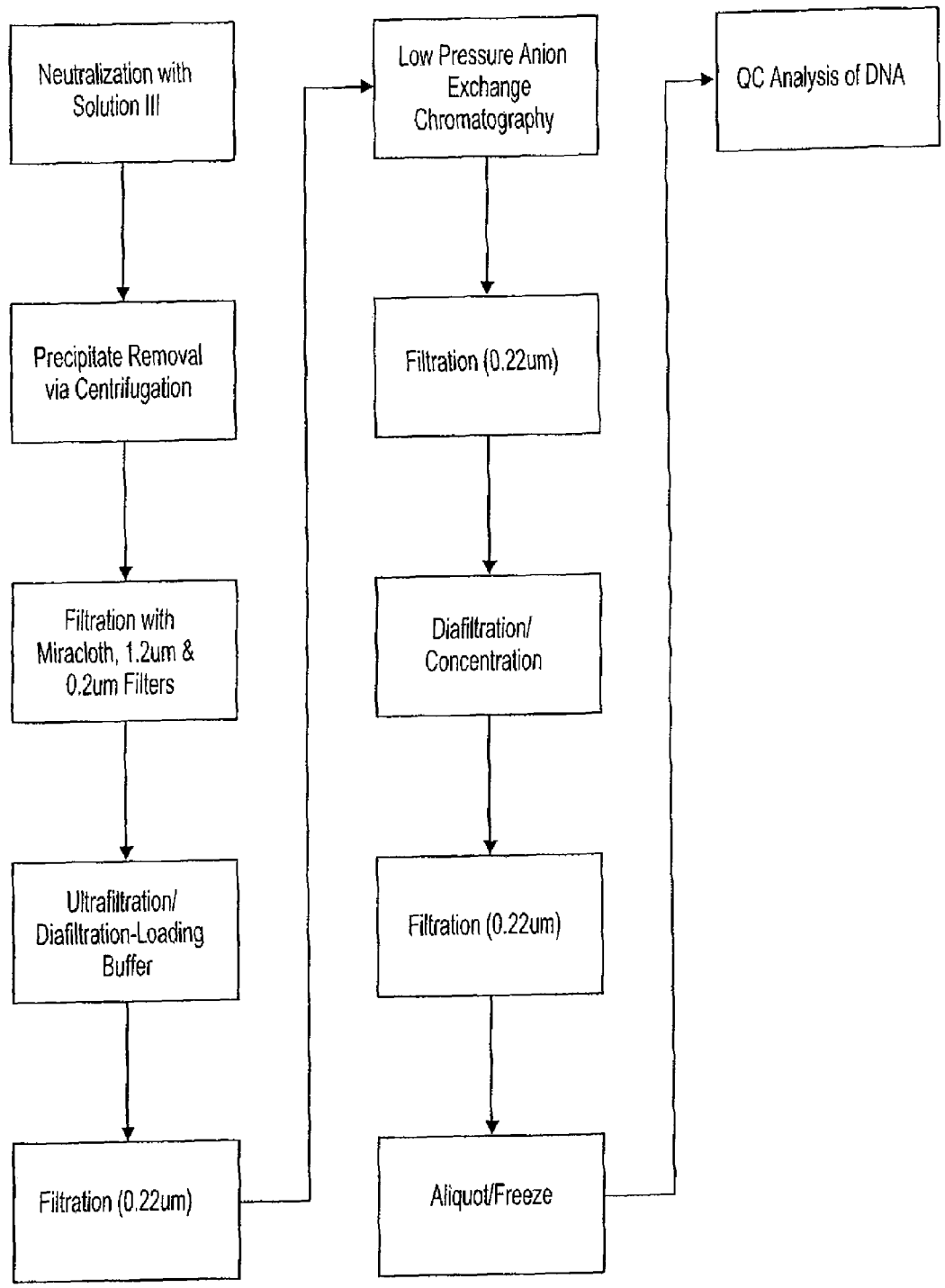

Pharmaceutical quality DNA was prepared as follows, using aseptic culture conditions for all cell culture procedures. FIG. 2 is a schematic representation of the procedural steps.

Figure 3:
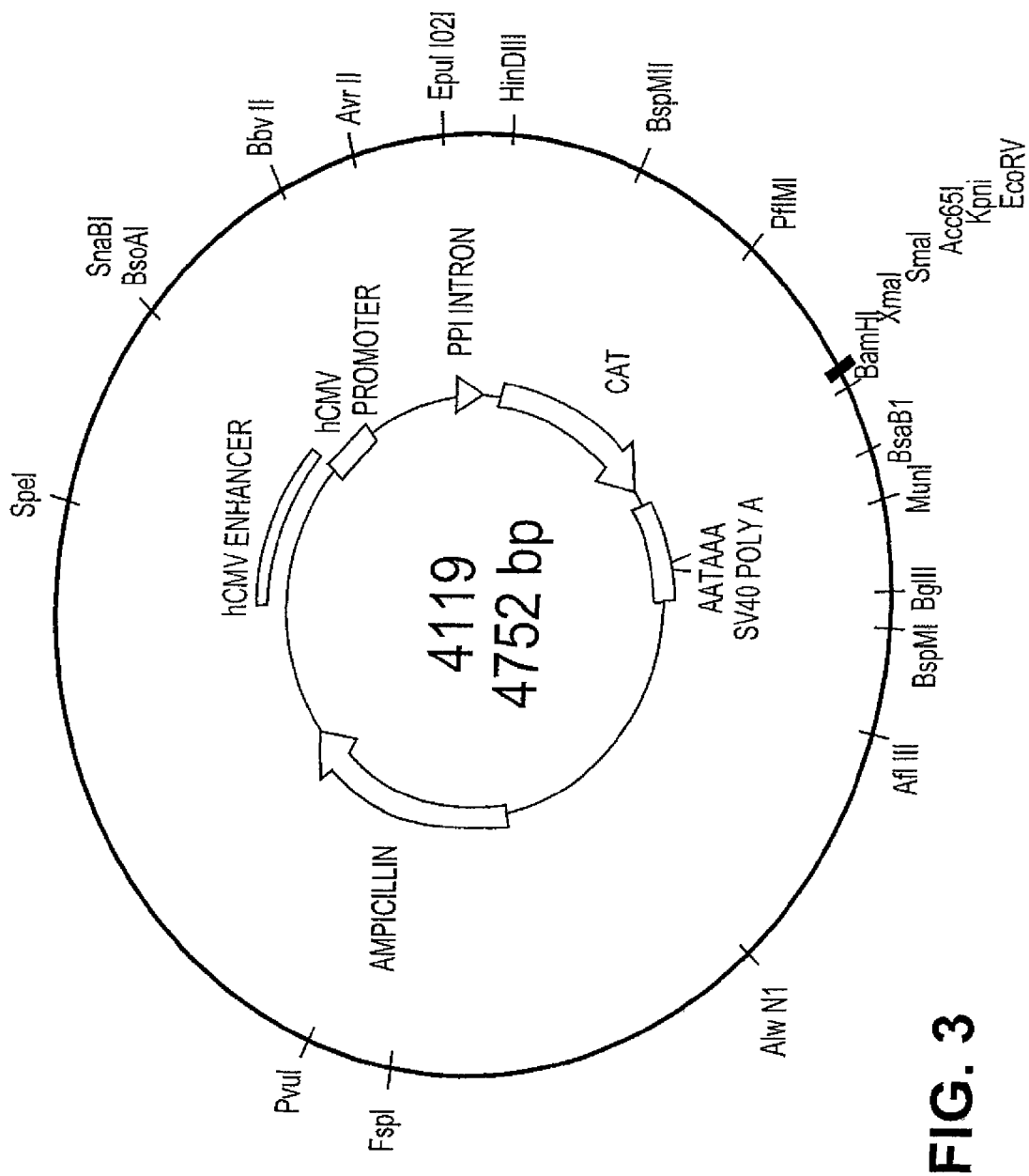
FIG. 3 is a schematic representation of the plasmid p4119.

An inoculum of *E. coli* containing plasmid p4119 (FIG. 3) was prepared from frozen stock by the addition of 1 ml of frozen (−80° C.) bacterial culture to a 500 ml foam-plugged flasks containing 100 ml TB broth (Sambrook et al., 1989) supplemented with carbenicillin (100 µg/ml). Cultures were incubated at 37° C. and shaken at 220 rpm for approximately 6 hours. Culture growth was determined by visual inspection or by determining $OD_{600}$, whereby OD values between 0.5 and 5 were deemed acceptable.

5 ml of this culture was used to inoculate each of 4 bioreactors containing 10 L TB media supplemented with carbenicillin (100 µg/ml) and with 1 ml/10 L Mazu DF204 antifoaming agent. These cultures were incubated at 3.7° C. and stirred initially at about 300 rpm. The cultures were aerated and dissolved oxygen was controlled via cascade control loops, agitation, airflow, and oxygen enrichment to an average of about 40% saturation. Cultures were incubated for about 10 to 16 h. After incubation, cell content of each culture was determined by $OD_{600}$; $OD_{600}$ values ranged from 16 to 18. Cells were harvested by centrifugation in a refrigerated Carr continuous flow centrifuge.

The cell pellets were spread into thin sheets and frozen at −80° C. until used for further plasmid purification. 3.2 Kg of the cell pellet was resuspended in 16 L Solution I (25 mM Tris-HCl, pH 8, 10 mM EDTA, 50 mM dextrose) at room temperature with stirring at 150 rpm for 1 h. RNase digestion was achieved by the addition of RNase (305 mg RNase/Kg cell paste) and incubating the solution on ice for 2 hours. Cells were lysed by the addition of the cells to 32 L Solution II (0.2N NaOH/1% SDS) in an ice bath. The solution is stirred using a Bow-Tie Stirrer (Cole Parmer, Vernon Hills, Ill.) for 25 min. This solution was then neutralized and cell debris and chromosomal DNA were precipitated by the addition of 16 L ice-cold Solution III (3M potassium, 5M acetate, pH 5.5). The solution was mixed with a Bow-Tie Stirrer on ice for 25 min.

The precipitated material was removed from the neutralized cell lysis solution by centrifugation. The solution was aliquoted into 1 L centrifuge bottles and centrifuged at 5300 rps for 20 min at 2° C. The supernatants were then decanted through two layers Miracloth (CalBiochem, La Jolla, Calif.) arranged at 90° to each other, into a container at room temperature. The decanted supernatants were then filtered through 1.2 and 0.2 µm filters arranged in series. As an alternative to centrifugation at this stage, precipitated material may be removed by filtration through a diatomaceous earth material such as Celite® HYFLO SUPER CEL® (Celite Corp., Lompoc, Calif.). See U.S. Pat. No. 5,576,196.

Filtered materials were then pumped into an ultrafiltration unit and the DNA solution filtered by tangential flow filtration through a Pall-Filtron Omega open channel Centrasette unit using 25 ft² of polyethersulfone (PES) membrane having a MWCO of 300K. The solution was introduced into the unit under a pressure of 10 psi, with the permeate channel open, and the solution allowed to circulate through the unit for about 50 min until a gel layer was formed. The permeate channel was then directed to a waste receptacle, and the DNA solution was filtered at a pressure of 10 psi until the solution was concentrated to a volume of about 3.6 L. Diafiltration buffer (Tris-HCl, pH 8.5) was then added and the solution was continuously diafiltered at a pressure of 10 psi, flow rate of about 1 L/min, until approximately 50 volume exchanges were performed.

After diafiltration, the retentate was recirculated through the ultrafilter for 10 min with the permeate valve closed. The retentate was removed and the membrane washed twice by an additional 1 L diafiltration buffer per wash for 10 min each, with the permeate valve closed. The wash solutions were added to the retentate and analyzed by HPLC and $OD_{260/280}$ analysis.

HPLC analyses were performed on a 4.6 mm×3.5 cm HPLC column packed with TSK-GEL DEAE-NPR resin at a buffer flow rate of 1 ml/min and monitored at 254 nm. Samples were diluted 1:20 with Buffer A (20 mM Tris-HCI, pH 8) and injected onto the column in a volume of 25 µl. Sample was eluted in a gradient of 0% Buffer B (20 mM Tris-HCI, pH 8/2M KCl): 100% Buffer A to 60% Buffer B: 40% Buffer A over 9 min. HPLC analysis of the permeate, and retentate containing plasmid DNA product showed that plasmid DNA was typically 95% pure, and often 100% pure as determined by HPLC at this stage.

Spectrophotometric analysis was performed at wavelengths of 250, 260, and 280 nm. Typical ratios for purified DNA are $OD_{260}/OD_{250}>1.1$, and $OD_{260}/OD_{280}>1.9$. A total of 2.307 g of plasmid DNA was isolated and purified in the above procedure, having $OD_{260}/OD_{250}$ of 1.1047 and $OD_{260}/OD_{280}$ of 1.9290.

The recovered plasmid DNA was filtered twice through a Gelman Ground Water Capsule 0.45 µm filter, followed by two filtrations through a Pall-Filtron Capsule $N_{66}$ 0.22 µm filter.

Plasmid DNA was further purified by ion exchange chromatography. DNA was loaded in a total volume of 4740 ml onto a Amicon Vantage A column packed with a 2.5 L bed volume of TMAE-650 (M) (trimethylamino ethyl) Fractogel (EM Separations, Gibbstown, N.J.). The column was equilibrated with Equilibration Buffer (50 mM Trist, pH 8.5) at a LFV (linear flow velocity) between 80-150 cm/hr at 0.7 bar column pressure. The DNA was loaded at 225 ml/min flow rate at 0.7 bar column pressure. The column was washed with 3 to 5 column volumes of Equilibration Buffer at 32-35 mS. DNA was eluted from the column over an elution gradient of from 32 mS to 59 mS or from 0.5M NaCI to 1.5M NaCl in 50 mM Tris, pH 8.5, at a flow rate of 225 ml/min and a column pressure of 0.55 bar. Fractions were collected in volumes of 130 to 1650 ml starting when the $A_{260}$ was greater than 0.2 and ending when $A_{260}$ was less than 0.2.

All fractions were analyzed by HPLC and LAL endotoxin assay. The results are shown in Table 1. A total of 2044 mg DNA was loaded onto the column and 1946 mg were recovered in a total volume of 6079 ml, a yield of 95.22%. Column fractions 2-10 were pooled (1905 mg DNA and $3.73 \times 10^5$ EU LPS in 5941 ml). Fractions to be pooled were chosen to provide the maximum yield of recovered DNA while minimizing the amount of contaminating lipopolysaccharide (LPS) in the preparation.

TABLE 1

| Fraction | DNA conc. (mg/ml) | Volume (ml) | Yield (mg) | LPS (EU/ml) | LPS/DNA (EU/mg) |
|---|---|---|---|---|---|
| 1 | 0.30042 | 137.59 | 41.33 | 263.7 | 878 |
| 2 | 1.04234 | 531.01 | 553.49 | 353.2 | 339 |
| 3 | 0.88851 | 501.18 | 445.30 | 103.2 | 116 |
| 4 | 0.62513 | 481.00 | 300.69 | 53.6 | 85.7 |
| 5 | 0.43912 | 529.82 | 232.65 | 38.8 | 88.4 |
| 6 | 0.26979 | 585.56 | 157.98 | 35.0 | 130 |
| 7 | 0.14750 | 526.13 | 77.60 | 15.3 | 104 |
| 8 | 0.08712 | 568.91 | 49.56 | 11.8 | 135 |
| 9 | 0.05810 | 603.83 | 35.08 | 9.12 | 157 |
| 10 | 0.03288 | 1613.78 | 53.06 | 6.49 | 197 |

The recovered DNA solution was filtered through a Pall Ultipor $N_{66}$ 0.2 µm filter. To reduce the salt content, the DNA solution was subjected to a final defiltration step using a Pall-Filtron Centramate open channel 100K MWCO membrane (2.0 sq. ft.). The filtration unit and membrane were first equilibrated with 1 L of a solution of 10 mM Tris-HCI, pH 8.0. The buffer is circulated across the membrane using a pump and a sterile reservoir bottle. The DNA solution was added with the permeate channel fully open, and the solution circulated for approximately 30 min at 10 psi. The DNA solution was then ultrafiltered until concentrated to a volume of approximately 100 ml. The concentrated solution was then diafiltered using continuous diafiltration against a solution of 10 mM Tris-HCI, pH 8, at 10 psi and permeate flow rate of 120 ml/min until the conductivity of the solution was decreased from an initial value of 35 mS to less than 1 mS (0.60) (buffer conductivity=0.53 mS). With the permeate valve closed, the rententate was then recirculated through the ultrafilter for 10 min. The retentate was then collected, and the membrane washed with three 100 ml washes of 10 mM Tris-HCI, pH 8.0.

The DNA and endotoxin concentrations of the diafiltered DNA solution and each of the washes was determined as above. The retentate and first wash were pooled, yielding 1.366 g DNA at a concentration of 5.564 mg/ml, and 90.35 EU/ml or 16.24 EU/mg DNA. This DNA solution was filtered through a Millipore Millipak 40 0.22 µm filter, followed by filtration of an additional 25 ml of final diafiltration buffer, and the two solutions pooled to yield the final product.

Yield of final plasmid DNA product from the final ultrafiltration was 80%. The final product was then aliquotted and stored at −20° C. until use. The final product was determined to meet the following Quality Control specifications:

| | |
|---|---|
| Color | clear to slightly cloudy |
| Endotoxin | <100 EU/ml |
| Purity | >95% by HPLC |
| DNA homogeneity | >90% ccc (covalently closed circular) |
| RNA | <2% by analytical HPLC |
| ssDNA | <1% by analytical HPLC |
| Protein | <0.1% by analytical HPLC, silver stain and SDS-PAGE |
| Genomic DNA | <1% by analytical HPLC and Southern Blot |
| Conductivity | <1 mS |
| pH | 7-8.5 |

Sterility was assayed by day 21 triptose broth culture showing no colonies. Identity was determined by restriction endonuclease digestion and analysis by agarose gel electrophoresis.

Example 2

The following example shows that either going at too slow a linear velocity through the static mixer or using too few mixing elements will result in poor mixing and poor lysis of the cells, leading to low product yields (Table 2 below).

TABLE 2

Effects of different flow velocities (shear rate) as a function of number of elements.

| Kenic Pipe Mixer | I.D. pipe Diam (in) | # of Elements | Velocity (ft/sec) | Viscosity (cps) | Shear Rate (sec$^{-1}$) | |
|---|---|---|---|---|---|---|
| | | | | | | After Lysis |
| Pipe 1 | 0.375 | 24 | 0.77 | 25 | 590 | well mixed |
| | 0.375 | 24 | 1.50 | 25 | 1156 | well mixed |
| | 0.375 | 18 | 0.77 | 25 | 590 | some heterogeneity |
| | 0.375 | 18 | 1.50 | 25 | 1156 | some heterogeneity |
| | | | | | | After Precipitation |
| Pipe 2 | 0.620 | 24 | 0.37 | 3 | 170 | uniformed, buoyant ppt |
| | 0.620 | 24 | 0.74 | 3 | 343 | uniformed, buoyant ppt |
| | 0.620 | 18 | 0.37 | 3 | 170 | uniformed, buoyant ppt |
| | 0.620 | 18 | 0.74 | 3 | 343 | uniformed, buoyant ppt |

Using 24 elements is optimal to achieve a well mixed homogenous system after the first mixing step (cell lysis by sodium hydroxide/detergent).

Example 3

The following example shows that using too high a linear velocity or too many mixer elements, especially in the second static mixer, will result in a finely divided precipitate due to too high a shear rate. The effect of too high a shear rate is that the quantity of contaminating genomic DNA in the final product is increased, and it can cause shear damage to the plasmid DNA. Table 3 shows the level of genomic DNA contamination, based on analyzing the outflow of the second static mixer by Southern blot analysis.

TABLE 3

Plasmid quality vs. linear velocity.

| Actual data w Kenic pipe mixer | Flowrate (lpm) | I.D. pipe Diam (in) | Viscosity (cps) | Reynolds | Velocity (ft/sec) | Shear rate (1/sec) | Genomic DNA concentration based on Southern blot (µg/ml) |
|---|---|---|---|---|---|---|---|
| | | | | | | No mixer (control) | >30 |
| | | | | | | w/ impeller (control) | >30 |
| Pipe 2 | 0.66 | 0.620 | 3 | 326 | 0.19 | 86 | 15-30 |
| | 1.31 | 0.620 | 3 | 646 | 0.37 | 171 | 7.5-15 |
| | 2.63 | 0.620 | 3 | 1297 | 0.74 | 343 | 7.5-15 |
| | 3.94 | 0.620 | 3 | 1944 | 1.11 | 514 | 7.5 |

Table 3 shows the genomic DNA content as a function of linear flow velocity in a 24 element static mixer. It appears that as the linear flow velocity increases, genomic content decreases due to increase mixing of the static mixers. Beyond an optimal linear flow velocity of about 0.7 to 1.1 ft/sec, however genomic content increases due to high shear rate. Precipitate generation at flow velocities higher than optimal show a smaller buoyant precipitate from sheared genomic DNA.

Example 4

The following example shows the effect of mixing velocity on plasmid DNA quality (determined by Southern blot analysis of the outflow from the second static mixer). The optimal number of elements depends, in part, on the flow rate. When too few elements are used and the velocity is too slow, plasmid DNA yield decreases and genomic DNA contamination increases. When too few elements are used and the velocity is too high, plasmid DNA yield decreases and plasmid-derived impurities increase. Similar results occur at a desired flow rate if too many elements are used (i.e., too much mixing).

The flow rate is selected to match that desired for centrifugation, while still maintaining high plasmid DNA yield and minimizing genomic DNA contamination. This allows the lysis, precipitation and clarification steps to be performed simultaneously, without interruption, and to be automated. In this case, when using laminar flow static mixers of the size used in this Example, the optimal flow rate is in the range of 0.7 to 1.1 ft/sec, with 24 elements.

TABLE 3

| Actual Data w Kenic pipe mixer | Flow rate (lpm) | I.D. pipe diam (in) | Reynolds | Velocity (ft/sec) | # of Elements | Shear rate (1/sec) | Genomic (ng/ul) |
|---|---|---|---|---|---|---|---|
| | | | | | no mixer control | | >30 |
| Pipe 1 | 0.25 | 0.375 | 24 | 0.19 | 12 | 147 | >60 |
| | 1.00 | 0.375 | 98 | 0.77 | 12 | 590 | >60 |
| | 3.00 | 0.375 | 294 | 2.30 | 12 | 1769 | 30-45 |
| Pipe 2 | 0.33 | 0.375 | 269 | 0.25 | 12 | 195 | |
| | 1.31 | 0.375 | 1068 | 1.01 | 12 | 772 | |
| | 3.94 | 0.375 | 3213 | 3.03 | 12 | 2323 | |
| Pipe 1 | 0.25 | 0.375 | 24 | 0.19 | 36 | 147 | 30-45 |
| Pipe 2 | 0.33 | 0.375 | 269 | 0.25 | 36 | 195 | |
| Pipe 1 | 3.00 | 0.375 | 294 | 2.30 | 36 | 1769 | >60 |
| Pipe 2 | 3.94 | 0.375 | 3213 | 3.03 | 36 | 2323 | |

Example 5

Purification by Direct Load of Clarified Lysate on to Anion Exchange Chromatography Column Approximately 40 L of fermentation broth yields about 2.2 kg of cell paste. After re-suspension of the cell paste, lysis and precipitation, approximately 40 liters of solution were ready for clarification by centrifugation. Centrifuging in a non-continuous centrifuge (Sorvall RC3b) at 7500×g for 25 minutes removed the solids and yielded a clarified product. Tris base (solid) was added to adjust the pH of the clarified product to 8.5 (a final concentration of 0.67 M). After Tris base addition, the conductivity decreased from 53 mS/cm to 50 mS/cm. The neutralized lysate was filtered in series with a nominal 0.2 μm glass filter (Sartorpure GF) and an absolute 0.2μ nylon filter (Pall Ultipor $N_{66}$) (5 ft² each) to reduce bacterial load and endotoxin levels.

The filtered lysate was then directly loaded (155 cm/hr linear flow velocity) onto an equilibrated (sodium chloride, 50 mM Tris, pH 8.5, 50 mS/cm) 1.5 liter TMAE Fractogel 650M column (13 cm diameter, 13 cm height) (EM Separations Technology, Wakefield, R.I., US Associate E. Merck, Darmstadt, Germany). The column was then washed with equilibration buffer for five column volumes (the $A_{260}$ reading was back to baseline). The column was further washed with three column volumes of 50 mM Tris-HCL, 1M NaCl pH 8.5 (56 mS/cm) to elute the endotoxin and genomic DNA. The plasmid DNA was then step eluted from the column using 50-90 mS/cm conductivity Tris/NaCl. The fractions containing high plasmid DNA levels were pooled.

The pooled product contained 1787 mg DNA, endotoxin level of 16 EU/mg, and 1.6% genomic DNA. The product was filtered again through 0.2μ nominal glass and 0.2μ absolute nylon filters described above. After filtering the product contained endotoxin level of 1 EU/mg and 0.18% genomic DNA, with 94% yield. The filtered product was diafiltered and subjected to a final 0.2μ sterilization filter as described in Example 1. The final product was 5.6 mg/ml, with 0.4 EU/mg and less than 0.2% genomic DNA.

The examples and embodiments described herein are for illustrative purposes only, and various modifications will be apparent to those of skill in the art, the invention to be limited only by the scope of the appended claims. All publications, patents and patent applications cited herein are hereby incorporated by reference as if set forth in their entirety herein.

What is claimed is:

1. A method for purifying plasmid DNA from a solution containing plasmid DNA, comprising the steps:
    a) contacting said solution with a precipitation solution;
    b) flowing the solution obtained in step a) through a static mixer under conditions of flow that provide Reynolds numbers in the range of about 50 to 500;
    c) further purifying said plasmid DNA using an open tangential flow ultrafiltration (TFU) under conditions that promote formation of a gel layer and said plasmid DNA is retained in a retentate solution;
    d) contacting said retentate solution obtained in step c) with an ion exchange chromatography resin under conditions in which plasmid DNA is bound to said resin; and
    e) eluting said plasmid DNA from said resin using a step gradient or a continuous gradient of a salt solution with increasing conductivity.

2. The method of claim 1, further comprising exposing said solution obtained by step c) to a ribonuclease (RNAase).

3. The method of claim 1, said ion exchange chromatography resin being an anion exchange chromatography resin.

4. The method of claim 1, said ion exchange resin being a strong anion exchange chromatography resin.

5. The method of claim 1, wherein said TFU is carried out using an ultrafiltration membrane having a molecular weight cutoff (MWCO) of 300 K Daltons, said plasmid DNA having sizes in the range of 2 Kb to 15 Kb being retained in said retentate solution.

6. The method of claim 1, wherein said TFU is carried out using an ultrafiltration membrane having a MWCO of 500 K Daltons, said plasmid DNA having sizes in the range of 15 Kb to 50 Kb being retained in said retentate solution.

7. The method of claim 1, wherein said TFU is carried out using an ultrafiltration membrane having a MWCO of 1000 K Daltons, said plasmid DNA having a size greater than 40 Kb being retained in said retentate solution.

* * * * *